(12) United States Patent
Ardizzone

(10) Patent No.: US 7,081,083 B2
(45) Date of Patent: *Jul. 25, 2006

(54) MAGNETO-CYMATIC THERAPEUTIC MATTRESS PAD

(75) Inventor: Vincent Ardizzone, Port Jefferson, NY (US)

(73) Assignee: Cymatics International, Inc., Port Jefferson, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 10/898,023

(22) Filed: Jul. 23, 2004

(65) Prior Publication Data

US 2005/0154249 A1    Jul. 14, 2005

Related U.S. Application Data

(63) Continuation-in-part of application No. PCT/US03/04546, filed on Feb. 12, 2003.

(51) Int. Cl.
*A61N 2/00*    (2006.01)

(52) U.S. Cl. .......................................................... 600/9

(58) Field of Classification Search .............. 600/9–15; 601/45–83, 89–93
See application file for complete search history.

(56) References Cited

U.S. PATENT DOCUMENTS 5,195,197 A * 3/1993 Gutierrez et al. .............. 5/500
5,642,739 A * 7/1997 Fareed ........................ 128/881
6,182,313 B1   2/2001 Eschenbach ................... 5/640

FOREIGN PATENT DOCUMENTS

| DE | 25 20 108    | 5/1975 |
| DE | 34 27373 A1  | 7/1984 |
| DE | 37 19331 A1  | 6/1987 |
| DE | 196 13 425 A1| 4/1996 |

OTHER PUBLICATIONS

Raphael, Cymatics Today with Elizabeth Colorio, Spirit of Ma'at: "Music of the Spheres", vol. 3, Oct. 2002.*

* cited by examiner

*Primary Examiner*—John P. Lacyk
(74) *Attorney, Agent, or Firm*—Orrick, Herrinton & Sutcliffe, LLP

(57) ABSTRACT

A mattress pad that delivers magnetic and cymatic therapy to a resting or sleeping human body. The device consists of a mattress pad composed of various comfort supporting materials incorporating interspersed throughout the pad small transducers to deliver cymatic vibrations and permanent magnets fixed at the center of each transducer to deliver magnetic field therapy. Both the cymatic vibrations and the magnetic field therapy are delivered to the limbs and organs of the body concurrently. The magnetic field also serves as a conduit for the cymatic vibrations providing a magnetic inductive coupling within the cells of the body which assists in restoring the cells to their healthy-state natural resonant frequency.

10 Claims, 3 Drawing Sheets

MAGNETO-CYMATIC THERAPEUTIC MATTRESS PAD

CROSS REFERENCE TO RELATED APPLICATIONS

This application is a continuation-in-part of P.C.T/U.S. patent application Ser. No. 03/04546 filed Feb. 12, 2003 which application is incorporated herein by this reference hereto.

BACKGROUND OF THE INVENTION

1. Field

The present invention relates to magneto-cymatic devices, more particularly a therapeutic mattress pad that can simultaneously apply magnetic therapy with cymatic therapy to limbs, organs and other parts of a resting or sleeping body.

2. State of the Art

The therapeutic use of devices delivering cymatic vibrations to treat certain ailments and debilitating conditions is known. Cymatic therapy is based on the principal that every cell in the body is enveloped by an electromagnetic field that resonates at its own particular sound frequency. Around 850 cymatic frequencies have been discovered over the years. When the body is well these frequencies are steady and constant, but any dysfunction or disease upsets the harmony of the body and the effected areas then generate off-resonance frequencies. Cymatic therapy aims to generate a frequency identical to that of healthy cells. The aim is to support what the cells are trying to do naturally, thereby aiding the healing process and restoring the body to good health and harmony.

The therapeutic use of magnetic fields in treating various conditions is also well known. The beneficial effects of applying a magnetic field to an area of human and animal anatomy such as the back, legs, arms and the like, are widely known and well documented. Magnetic fields are commonly used for therapeutic purposes such as reduction of inflammation in tissues and pain relief. Although it is not entirely clear how magnetic therapy works, it has been found to increase blood flow and therefore oxygen carrying capacity, to change the migration of calcium ions to or from the bone, to alter the pH balance of various body fluids, to alter hormone production from endocrine glands and to alter the enzymatic activity and other biochemical processes of the human body.

Many therapeutic devices are available which apply magnetic therapy to an anatomical area such as the muscles of the lower back to enhance circulation and relax such muscle. The use of magnetic mattress pads in the application of magnetic therapy is also known. Ardizzone in U.S. Pat. No. 6,626,820 discloses a magnetic mattress pad to provide therapeutic and restorative treatment to limbs, organs and other parts of the body.

Many therapeutic devices are known which combine magnetic therapy with vibratory massage, heat, infrared, or sound, or a combination of same. Ardizzone in U.S. Pat. No. 6,383,129 discloses a magnetotherapeutic device which combines magnetotherapy in conjunction with infrared therapy. Souder in U.S. Pat. No. 6,231,497 discloses a magnetic therapy device which combines a dynamic magnetic field in conjunction with vibratory massage. Eschenbach in U.S. Pat. No. 6,182,313 discloses a magnetic therapy head cradle apparatus which combines a sound system in the head cradle with the magnetic field. Franco-Vila in U.S. Pat. No. 4,177,796 discloses a magnetic thermal vibrational device which simultaneously applies electromagnetic alternating directional energy, thermal, and vibrational energy to various areas of the body to reduce or eliminate the pains and symptoms of arthritis.

Although these various prior art devices apply magnetic therapy in combinations with vibration, heat and sound, none of the prior art devices apply a magnetic field in conjunction with cymatic vibration. Although both magnetic therapy and cymatic therapy have each been utilized to treat an affected area, the combination of the two therapies delivered by a therapeutic mattress pad device of the present invention provides additional beneficial effects to the user as the entire body receives both cymatic vibrational therapy to re-establish cellular resonance to treat various conditions and magnetic stimulation to enhance blood flow. Cymatic frequencies are delivered both by mechanical vibration and by the vibrating magnetic field by inductively linking with the cell's own electromagnetic field. This novel combination of cymatic vibrations with a magnetic field in a mattress pad provides a superior mode of therapy that can conveniently be applied for a period of several hours over the entire body while the person rests or sleeps without interfering with a person's daily activities.

SUMMARY OF THE INVENTION

A magneto-cymatic mattress pad simultaneously providing magnetic and cymatic therapy while a person rests or sleeps is disclosed herein. Broadly, the invention relates to a mattress pad comprising any comfort support material which contains cavities that house at least one rare earth permanent magnet coupled to a transducer that converts cymatic sound frequencies to mechanical vibrations, and a Central Processing Unit ("CPU") that produces electrical signals at selected cymatic sound frequencies that is electrically connected to the transducer. A preferred embodiment of the invention provides a flexible mattress pad that can be used on top of any conventional mattress or waterbed, comprising a comfort support material containing an array of cavities that contain rare earth magnets each coupled to a transducer that is connected to a CPU. This preferred embodiment of the invention provides a transportable apparatus for treating various injuries, disorders or disease conditions, comprising a thin flexible mattress pad device capable of being rolled up for carrying and capable of generating cymatic vibrations simultaneously with a strong magnetic field at one or more positions throughout the mattress pad and locatable in direct contact with the head, limbs and joints of the body. Advantageously, the present invention provides a therapeutic device capable of delivering treatment while the person is resting or sleeping on it and provides vibrations corresponding to an adjustable range of cymatic frequencies in combination with magnetic therapy.

OBJECTS OF THE INVENTION

It is therefore, an object of the present invention to provide a magneto-cymatic mattress pad which generates a magnetic field currently with cymatic vibrations at a selected frequency or at a plurality of frequencies in accordance with the requirements of the operator.

It is yet another object of the invention to provide magneto-cymatic therapy while one rests or sleeps.

These and other objects and advantages of the present invention will be apparent from a review of the following specification and drawings.

BRIEF DESCRIPTION OF THE DRAWINGS

Further features, benefits, and advantages of the present invention will be apparent from a review of the following detailed description and accompanying drawings, in which like reference characters refer to like elements, and in which.

DETAILED DESCRIPTION OF THE INVENTION

The detailed description set forth below in connection with the appended drawings is intended as a description of presently preferred embodiments of the invention and is not intended to represent the only forms in which the present invention may be constructed and/or utilized. The description sets forth the functions and the sequence of steps for constructing and operating the invention in connection with the embodiments which are described for purposes of illustration and not of limitation. However, it is to be understood that the same or equivalent functions and sequences may be accomplished by different embodiments that are also intended to be encompassed within the spirit and scope of the invention, and that particular values and measures may be varied without departing there from.

Figure 1:
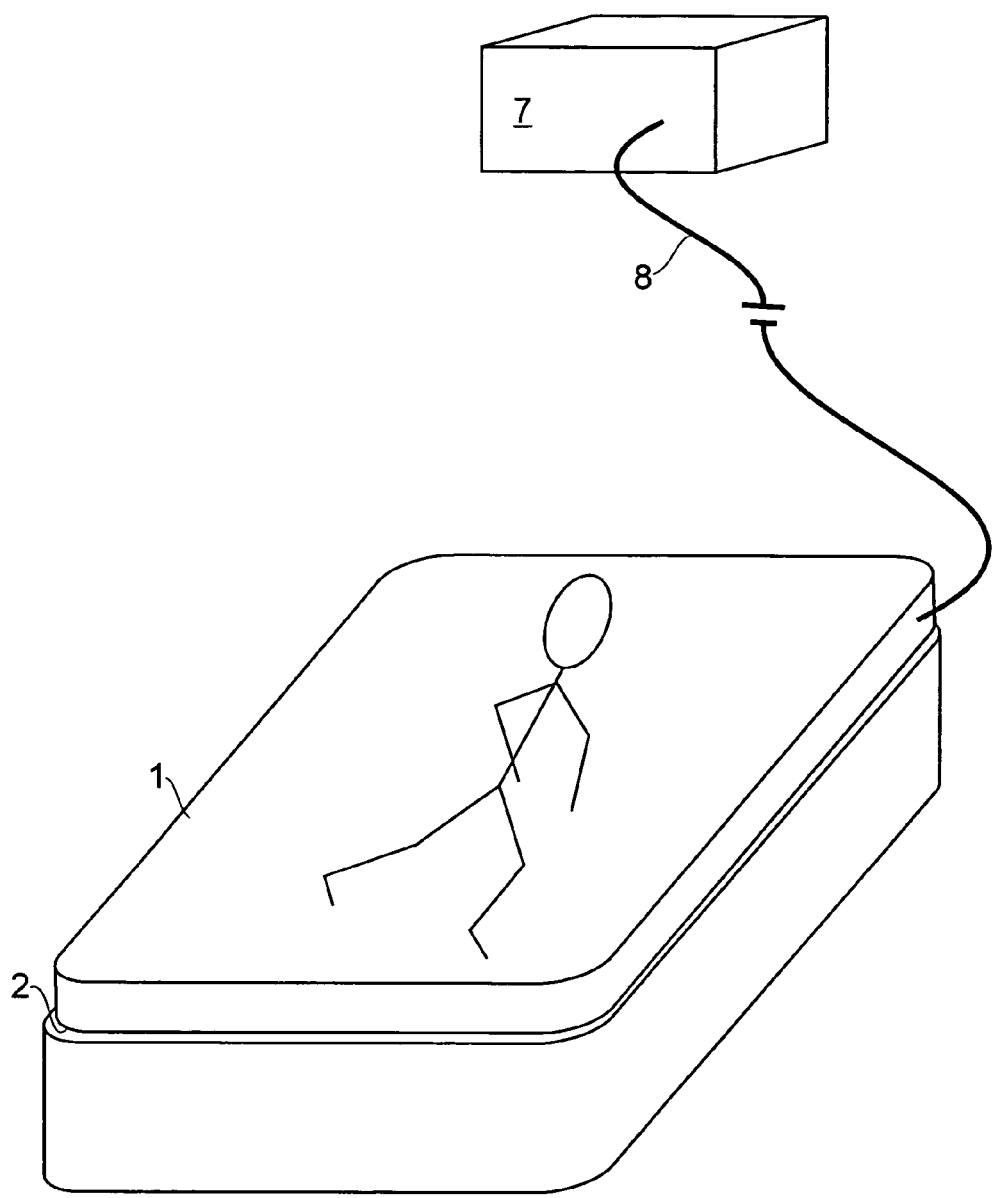
FIG. 1 is a perspective view of the magneto-cymatic mattress pad.
Figure 2:
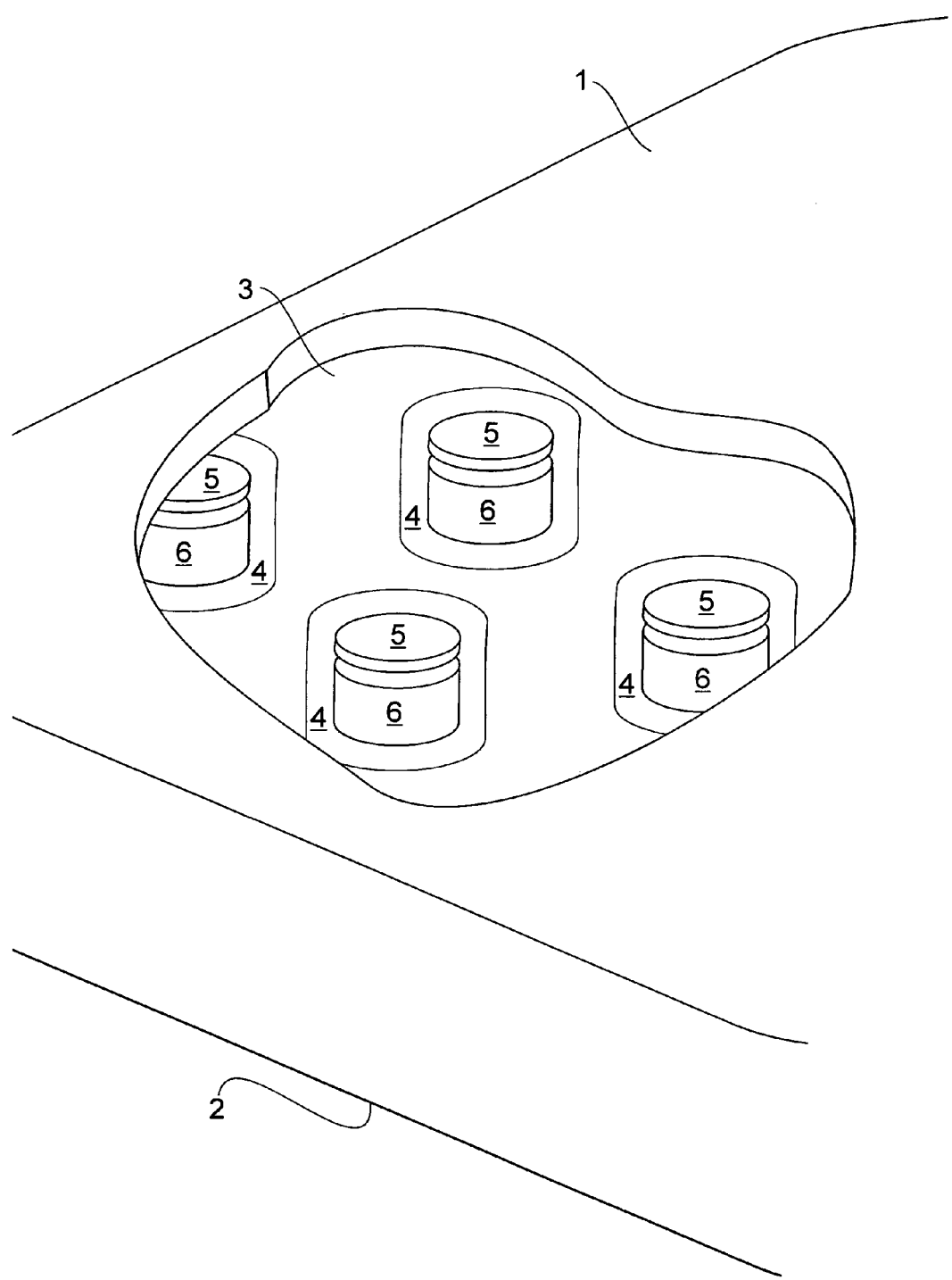
FIG. 2 is a magnified view of coupled magnets and transducers housed in cavities within the mattress pad device.

The Figures show different views of the preferred embodiments of the magneto-cymatic therapeutic mattress pad of the present invention. The preferred embodiment of the present invention is a mattress pad which may be a flexible pad that is capable of use on top of any conventional mattress or a waterbed. Another embodiment of the invention provides the array of magnets coupled in transducers integrated as a permanent part of a full sized mattress. The invention is applicable to a wide variety of disorders and disease conditions such as headaches, musculoskeletal injuries, arthritic joint conditions and back pain and provides for treating such conditions by positioning the therapeutic apparatus of the invention directly beneath the resting or sleeping body. In the preferred embodiment, with reference to FIGS. 1 and 2, the mattress pad has a upper surface (1) and a lower surface (2) made of a flexible non-magnetic material surrounding an interior cushioning or supportive material (3) that contains spaced apart cavities (4) each of which houses a powerful permanent magnet (5) closer to the upper surface—and which is coupled to a transducer (6) positioned closer to the lower surface of the mattress pad (2). In another embodiment the magnet-transducer couplets may be interspersed throughout a rubber or foam-like material.

The magnetic field provided by the preferred embodiment of the present invention has a magnetic strength in the mattress pad within the range of 300 to 3000 gauss, preferably 3000 gauss, as measured at the magnet surface by a Gaussmeter and is generated by a strong permanent magnet selected from such materials as neodynium (Nd), samarian cobalt, ferrite, or alnico. Neodynium is preferred as it provides the most powerful magnetic material. An electric coil may be used instead of a permanent magnet to produce an oscillating electromagnetic field; further providing the ability to produce a magnetic field of variable strength. However, the level of current required to produce a magnetic field of comparable strength to a high power permanent magnet is not as practical because the size of wire and number of turns required would adversely effect the operation of the transducer mechanism. In the preferred embodiment the magnetic field will concurrently oscillate at the prescribed cymatic frequencies.

The cymatic frequencies are generated from electrical signals produced at audio frequencies by a Central Processing Unit (7) and transmitted to each transducer (6) contained within the mattress pad. Each transducer (6) converts the electrical signals to mechanical vibrations which cause the upper surface (1) to oscillate according to selectable sound wave (cymatic) frequencies, and thereby provide cymatic treatment when the mattress pad device is applied directly in contact with the body being treated. The cymatic frequencies are preferably preset. The magnetic filed emanating from the mattress pad device vibrators at the frequencies generated by the transducer, and can penetrate the tissue and deliver cymatic therapy in conjunction with magnetic therapy by induction with the electromagnetic frequency of the tissue being treated in addition to any mechanical vibration of the mattress pad upper surface. The simultaneous application of the strong magnetic field with the cymatic vibrations will produce additional stimulation to the underlying tissue that the mechanical cymatic oscillations of the mattress pad alone or the magnetic field alone cannot produce.

Each magnet (5) will be coupled securely to each transducer (6) as close to the upper surface of the mattress pad device (1) as practical.

The mattress pad device may be flexibly connected to the Central Processing Unit (7) by means of an electric cable (8).

Figure 3:
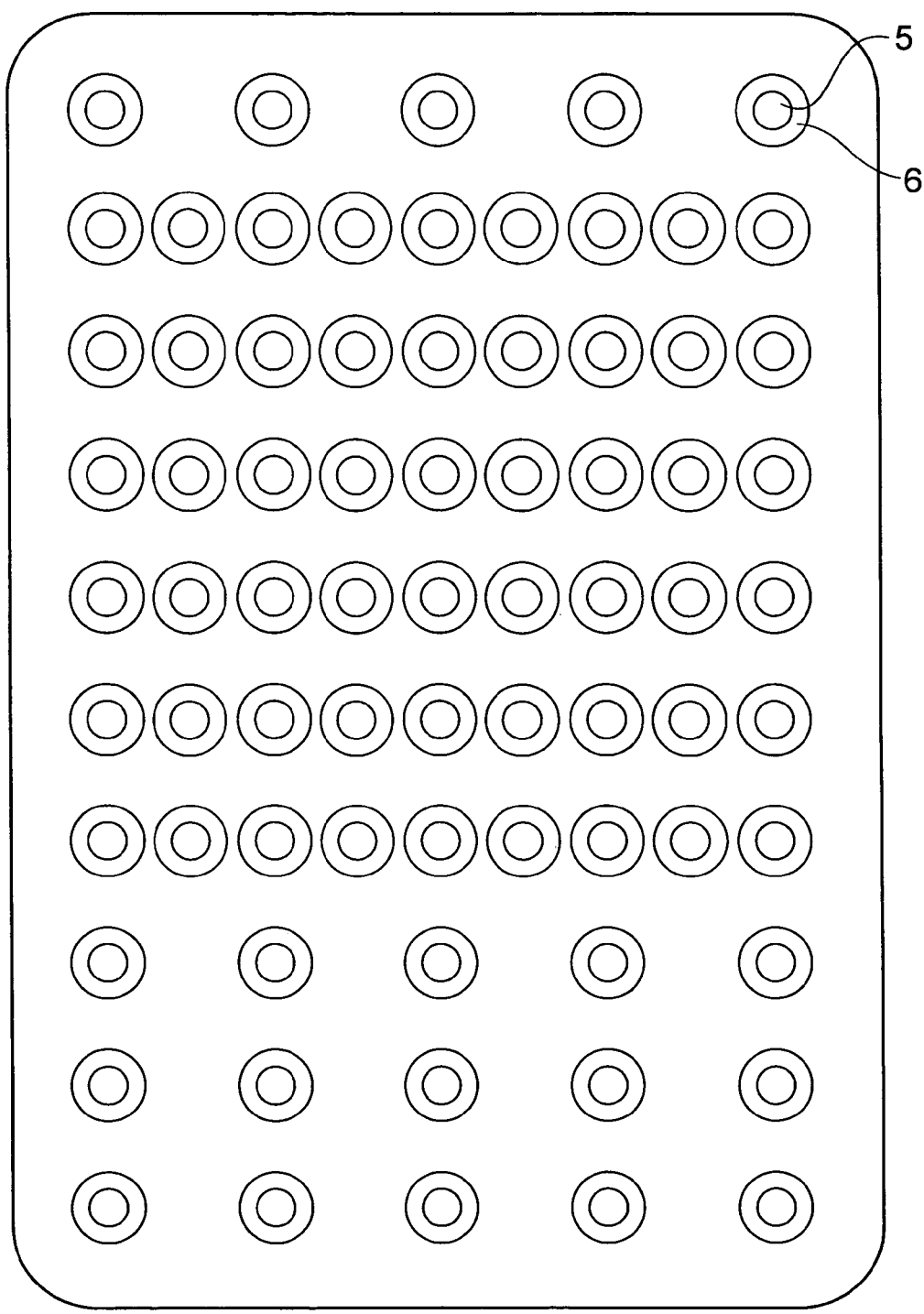
FIG. 3 shows how the multiple magnets and transducers may be arranged in an array within the mattress pad of FIG. 1.

In order to enhance such magneto-cymatic therapy the array of magnets and transducers may be arranged more closely together in the region of the mattress pad to be positioned under the torso of the person being treated. The arrangement shown in FIG. 3 permits the therapy to be concentrated where it will have the greatest affect on organs such as the liver, heart, kidneys and lungs.

I claim:

1. A mattress pad for providing concurrent magnetic therapy and cymatic therapy to the body, comprising:
    an array of magnets, each of said magnets providing a magnetic field;
    an array of transducers, wherein each of said transducers has a signal input and an operating state in which said transducer vibrates at a selected frequency responsive to said signal input;
    a central processing unit having an electrical signal output, said electrical signal output being selectable from among a range of audio frequencies wherein said array of transducers' signal inputs being coupled to said central processing unit's electrical signal output and said array of transducers being mechanically coupled to said array of magnets wherein said array of transducers convert said central processing unit's electrical signal at said audio frequency to mechanical vibrations at said frequencies; and
    whereby, simultaneous application of magnetic therapy and cymatic therapy occurs when said array of magnets is placed in proximity to tissue to be treated and vibrated by said array of transducers.

2. The mattress pad of claim 1, further comprising a support material wherein said array of magnets and said array of transducers are housed within said support material.

3. The mattress pad of claim 2, wherein said support material comprises a flexible non-magnetic material.

4. The mattress pad of claim 3 wherein said array of magnets and said array of transducers comprises a ratio of one transducer associated with one magnet.

5. The mattress pad of claim 4 wherein said support material is thin enough to permit the mattress pad to be rolled up and carried.

6. The mattress pad of claim 4 wherein said arrays of magnets and transducers are arranged throughout the mattress pad in a manner that provides therapy concentrated in the region of the torso of a body resting or sleeping thereon.

7. The mattress pad of claim 6, wherein the magnets are selected from among the group consisting of neodymium, Samarian cobalt, ferrite, alnico and combinations thereof.

8. A method of administering magneto-cymatic therapy to the entire body of a person to treat injuries, disorders and diseases comprising: positioning the body on top of an array of magnets in proximity to the body to be treated and vibrating said positioned array of magnets at a first frequency for an effective amount of time; and vibrating said positioned array of magnets at a first frequency mechanically vibrated at said first frequency to provide simultaneous application of magneto therapy and cymatic therapy.

9. The method of claim 8 wherein vibrating said array of magnets further comprises providing a central processing unit and a plurality of transducers, the central processing unit having a plurality of electric signal outputs corresponding to a plurality of cymatic frequencies, coupling said central processing unit to transducers capable of converting said electric signals to mechanical vibrations at said cymatic frequencies, coupling said transducers to said array of magnets, and selecting said electrical signal outputs and thereby vibrating said array of magnets at the frequencies corresponding to said selected electric signals.

10. The method of claim 9 which further comprises administering said magneto therapy and cymatic therapy to the whole body during several hours while the person being treated is resting or sleeping.

\* \* \* \* \*